May 27, 1941. C. L. FITZGERALD Plant Pat. 469
ROSE
Filed Dec. 7, 1940
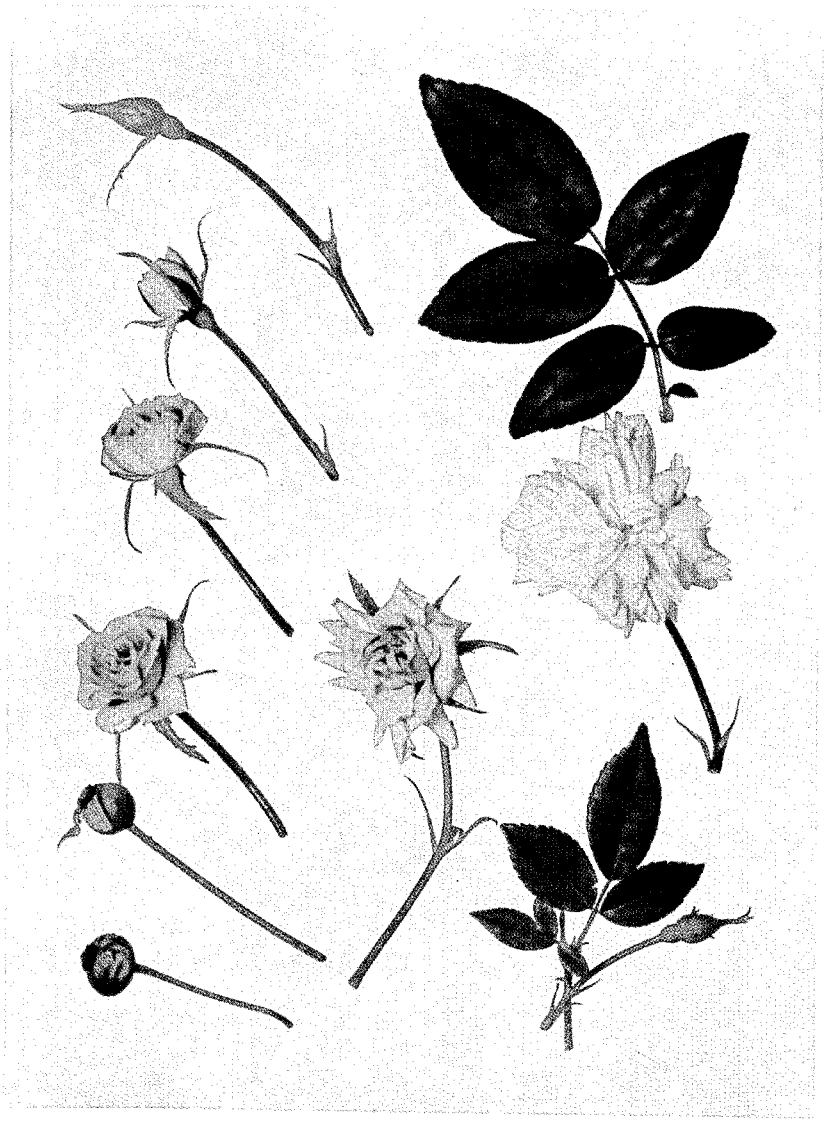
INVENTOR:
CHARLES L. FITZGERALD,
BY Alfred W. Knight
ATTORNEY.

Patented May 27, 1941

Plant Pat. 469

UNITED STATES PATENT OFFICE

469

ROSE

Charles L. Fitzgerald, Hawthorne, Calif.

Application December 7, 1940, Serial No. 369,088

1 Claim. (Cl. 47—61)

My invention relates to improvements in "baby" roses, and pertains particularly to a pink rose of a size comparable to the well-known Cecil Brunner, but differing therefrom in color of flower and in certain other particularities. The variety of rose of the present invention is the result of hybridization and cross-hybridization from hybrid highly colored roses of my own development, and the Cecil Brunner. These hybrid highly colored roses were developed between 1911 and 1926, and the small well colored roses from these plants were cross-bred with a bush Cecil Brunner as a mother. The well-developed crosses from this hybridization were bred and cross-bred to and with Cecil Brunner, with the realization of the present variety in 1937.

The parent seedling of the present variety was grown under glass until it was about six inches tall, was then transplanted and has since been growing outside, at a location near the city of Los Angeles, California, within a few miles of the Pacific Ocean and within the so-called "fog-belt." This variety has been found to reproduce asexually true to type and character.

The accompanying color plate shows the development of a bloom from a bud through the full-open stage, together with leaves in various stages of development.

The following is a detailed description of my new rose. Where references are made herein to colors, by plate and number, it will be understood that the reference is to the corresponding plate and color patch of "A Dictionary of Color" (Maerz and Paul, McGraw-Hill, 1930). Where a color name is given in parentheses, following the plate and number, that name is the one ascribed by Maerz and Paul as being the most common name for such color.

The instant rose is a good bloomer, after the winter rest. Some buds and flowers remain on the bush until late November. It is a heavy bloomer after the winter rest and in late summer, tapering off in bloom in late fall weather. The rose is resistant to mildew, rust and black spot.

The rose is an upright or bush type, of good growing habits. The foliage is thick upon the bush. The leaf-branch is unequally pinnate, and when mature is comprised of five to seven shortly-stalked fingers or leaflets, the laterally extending leaflets being quite uniformly spaced along the petiole. The over-all length of the mature leaf-branch is about four inches, and the over-all width is about three inches. The texture of the leaves is rather firm, and slightly glossed. The color of the leaves varies between Plate 23, J—8 (Mt. Vernon Green) and Plate 24, L—1 (Brewster Green++). Two adnate stipules occur on each leaf. The leaflets are prolate, without markedly apiculate apices except on new leaflets, the more mature leaflets being tapered gently to the apex. The leaflets have a pronounced longitudinal convexity which is accentuated near the apex, as well as a pronounced lateral convexity either side of the midrib. The leaflets are serrate, the points of the serrations being directed forwardly and being spaced from one-sixteenth to one-eighth of an inch apart along the length of the edge. The new and old wood are the same color approximating Plate 23, L—4 (Quaker Green).

The plant presents very few thorns, the color of which when young approximates Plate 6, L—10 (Cuba+). They occur singly, and on the canes only, and then considerably separated from one another. No short needles or prickles occur on either the wood or the under side of the leaflets. Such thorns as do occur are about three-eighths of an inch long, and sharp.

*The flower*

The bud just prior to opening is about three-eighths of an inch in diameter and about one inch long from the tip of the sepals to the base of th calyx, i. e., to the juncture of the calyx with the peduncle. The color of the inside of the sepals is approximately that of Plate 18, C—6 (Olivine) and that of the outside and of the calyx is that of Plate 15, L—4 (Olive Green). The peduncle is stipulate (two or three adnate stipules) and is from one and one-half to one and three-quarters inches long.

The color of the petals upon opening approximates Plate 2, K—4, shading to Plate 9, K—7 at the base; a pin stripe of the base color frequently extends to the apex of the petal on the outside. As the bud opens, the color becomes more pink, approaching Plate 2, H—5 to Plate 2, D—4, and fading to as light as Plate 2, A—3 just before dropping off. A pin stripe of Plate 2, A—7 frequently extends lengthwise of the center of the petal. As the flower matures, the form becomes slightly oval, with the petals curling back to some extent; the petals also curl at the edges near the apex, producing a conically pointed effect. The fully extended blooms average one and one-quarter to one and one-half inches in diameter, and are usually borne in clusters averaging three blooms. The permanence is good, and the color persists even in the open. When the flowers are picked for inside bouquets, the colors remain much more distinct. The blooms occurring in the late fall show somewhat deeper pink coloring. The above colors were observed in July. The petalage is double, in arrangement of eight rows. The rose has no discernible fragrance.

*Genital organs*

The stamens and anthers are well concealed until the rose approaches the full-blown stage, and even then some of the inside petals curl inwardly and partly conceal the same. The stamens are the color of Plate 9, J—8 (Genista), with filaments of Plate 2, A—10. The pollen is colored that of Plate 10, L—7 (Golden Yellow); the styles are the color of Plate 5, K—5 (Hollywood); the stigmas are the color of Plate 10, J—1 (Sulphur Yellow) and the stigma filaments are the color of Plate 3, J—4.

*The fruit*

The mature fruit is coarsely rugose, a prolate spheroid in shape, some one-half inch in diameter and about three-eighths of an inch long. The sepals usually dry up and fall off or are blown away by the wind, leaving a cup-shaped calyx end which is approximately three-sixteenths of an inch in diameter. The color of the mature fruit is approximately that of Plate 7, L—7 (Maroon), the sepals attaining the color of Plate 7, J—7 (Roan) prior to dropping off. The fruit is for the most part fertile.

I claim:

The variety of non-fragrant hybrid bush baby rose herein shown and described, characterized particularly in its deep pink coloring on the inside of the petals, its rich golden yellow coloring on the outside of the petals as they are shaded to the base, its substantial freedom from thorns and its complete freedom from needles and prickles, its resistance to disease, particularly to mildew, rust and black spot, and its fertile fruit.

CHARLES L. FITZGERALD.